US008424782B1

(12) United States Patent
Heff et al.

(10) Patent No.: US 8,424,782 B1
(45) Date of Patent: Apr. 23, 2013

(54) AEROSOL TRANSPORT SYSTEM

(75) Inventors: Allan Heff, Newton, MA (US); Raymond S. Uttaro, Lexington, MA (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 153 days.

(21) Appl. No.: 12/873,417

(22) Filed: Sep. 1, 2010

(51) Int. Cl.
*B05B 1/34* (2006.01)

(52) U.S. Cl.
USPC ............................................ 239/463; 239/11

(58) Field of Classification Search ................ 239/1, 11, 239/589, 593, 597, 601, 463, 466, 468
See application file for complete search history.

(56) References Cited

U.S. PATENT DOCUMENTS

| | | | | | |
|---|---|---|---|---|---|
| 3,074,199 | A | * | 1/1963 | Johnson et al. | 43/129 |
| 3,242,098 | A | * | 3/1966 | Andrews | 422/305 |
| 3,305,144 | A | * | 2/1967 | Beres et al. | 222/402.13 |
| 4,013,396 | A | * | 3/1977 | Tenney | 431/11 |
| 4,818,843 | A | * | 4/1989 | Swiatosz | 392/397 |
| 6,595,437 | B1 | * | 7/2003 | Lawson et al. | 239/119 |

* cited by examiner

*Primary Examiner* — Davis Hwu
(74) *Attorney, Agent, or Firm* — AFMCLO/JAZ; Chastity Whitaker

(57) ABSTRACT

An aerosol transport system. The aerosol transport system comprising a tube and having a plurality of windings that permit the flow of aerosols, including particles, there-through so as to compensate for gravity and/or centrifugal forces and reduce the settling of particles within said tube.

6 Claims, 3 Drawing Sheets

AEROSOL TRANSPORT SYSTEM

STATEMENT OF GOVERNMENT INTEREST

The invention described herein may be manufactured and/or used by or for the Government for governmental purposes without the payment of any royalty thereon.

FIELD OF THE INVENTION

This invention relates to transporting aerosol over horizontal, or near horizontal distances, in a tube with reduced particle settling in such tube.

BACKGROUND OF THE INVENTION

In many situations, it is desirable to transport aerosol over long distances. For example, aerosol collectors may be mounted in one location and aerosol detectors may be mounted elsewhere. Or it can be desirable to multiplex one detector to many collectors. Current means for transporting aerosol particles horizontally are limited. Generally, particles with diameters larger than 5 microns can only be transported for limited distances or with very low transport efficiency. Typical transport means are a straight tube. Straight tubes transport small particle sizes efficiently only over limited distances. Losses in straight tubes are high due to competing mechanisms. At low speeds, gravitational sedimentation dominates. At high speeds, turbulent inertial losses dominate. If there are bends in the tube path, there will be losses at the bends at high speeds.

Aerosol particles traveling with the flow in a straight, horizontal tube are subject to deposition on the tube inner surfaces due to gravitational settling. In laminar flow, significant particle deposition can occur. Particle deposition is a technical challenge, especially for the transport of larger particles. Meaning that, at low speeds and in laminar flow, the only important deposition mechanism is that of gravity. This mechanism is called gravitational settling.

In conventional aerosol transport systems considerable settling of particles is inevitable and, in long distances, can exceed 50% of the conveyed particles, impairing the effectiveness of such transport.

Accordingly there is need and market for an aerosol transport system having a tube that reduces gravitational settling of particles and otherwise overcomes the above prior art shortcomings.

SUMMARY OF THE INVENTION

Broadly, the present invention provides a method of reducing the settling of particles during transport of an aerosol in a tube over long distances and includes configuring the tube in a coil about a least one axis that is substantially horizontal and flowing the aerosol along the tube in a winding path so as to compensate for gravity to reduce the settling of particles on the interior walls of the tube.

The invention further provides a method for reducing such settlement of particles by flowing the aerosol through a tube configured in countervailing helical paths so as compensate for gravity and centrifugal forces and reduce settlement of the particles within the tube.

The invention further provides an aerosol transport system employing a tube having a plurality of coils or windings that permit the flow of aerosols, including particles, there-through so as to compensate for gravity and/or centrifugal forces and reduce the settling of particles within said tube.

DEFINITIONS

By long distances as used herein, is meant a length of tube at least 10 times its diameter.

By substantially horizontal as used herein, is meant a tube that is wound about an axis that is predominately horizontal, or nearly so, over its length but which axis can have up and down gradients along the way.

BRIEF DESCRIPTION OF THE DRAWINGS

The invention will become more apparent from the following detailed specification and drawings in which.

DESCRIPTION OF PREFERRED EMBODIMENTS

Referring to the present invention in detail, one can consider a particle 8 in a small volume of fluid slug 10. The slug 10 is large compared to the size of the particle 8, but small compared the length scale of the tube, per FIG. 1. In this figure, g is the gravitational force, n is the orientation of a chosen surface on the fluid slug 10, and v is the fluid velocity. Because the fluid flow is laminar, the particle 8 moves with the fluid slug 10, except as affected by external forces, such as gravity, acting upon it.

Figure 2:
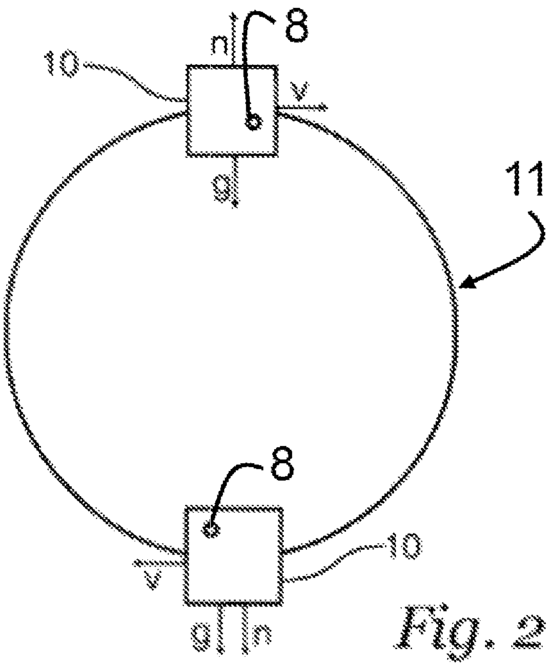
FIG. 2 is a schematic, cross-sectional view of an aerosol unit according to the method of the present invention.

In practical scenarios, the gravitational force on the particle 8 is always present. However, the time average gravitational force in the reference frame of the slug 10 can be reduced to zero. This is done by rotating the slug 10, with its axis of rotation, substantially horizontal, per FIG. 2. FIG. 2 shows flow around a cylinder 11. When the slug 10 is at the top of the cylinder 11, gravity accelerates the particle 8 downward in the reference frame of the slug 10 (in a direction opposing the vector n). When the slug 10 is at the bottom of the cylinder 11, gravity accelerates the particle 8 upwards in the reference frame of the slug 10 (in a direction parallel to the vector n).

Figure 3:
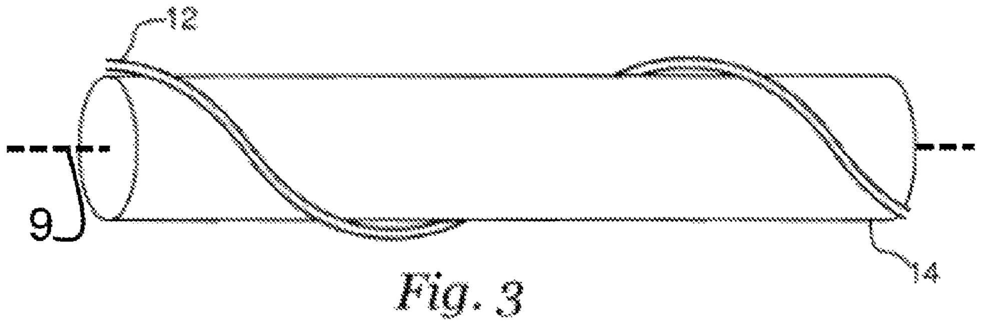
FIG. 3 is a fragmentary, side elevational view of a tube winding embodying the present invention.

One can apply the above method of a rotating fluid slug to minimize settling of particles in laminar flow through a substantially horizontal tube. For example, in FIG. 3, the tube 12 is wound in a coil around a guide cylinder 14. The total fluid path is only slightly larger than the helical circumference of the cylinder 14, when the coil of the tube 12 is so wound.

Figure 1:
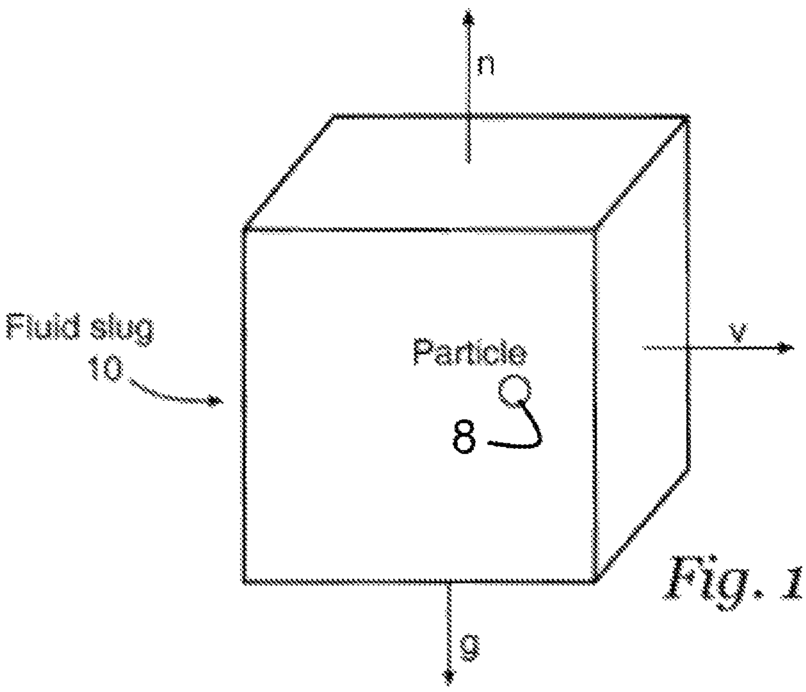
FIG. 1 is a schematic view of an aerosol unit having a particle therein affected by certain vectors in aerosol flow.

The winding path of the fluid introduces a centrifugal force on the particle 8 (FIG. 1). This force is directed at all times towards an outer wall within the tube 12, where the outer wall is considered the wall farthest from a coil axis 9. Although deposition due to gravity has been removed from the system, the newly introduced centrifugal force will cause particles 8 (FIG. 1) to deposit on an interior of the outer wall of the tube 12.

Figure 4:
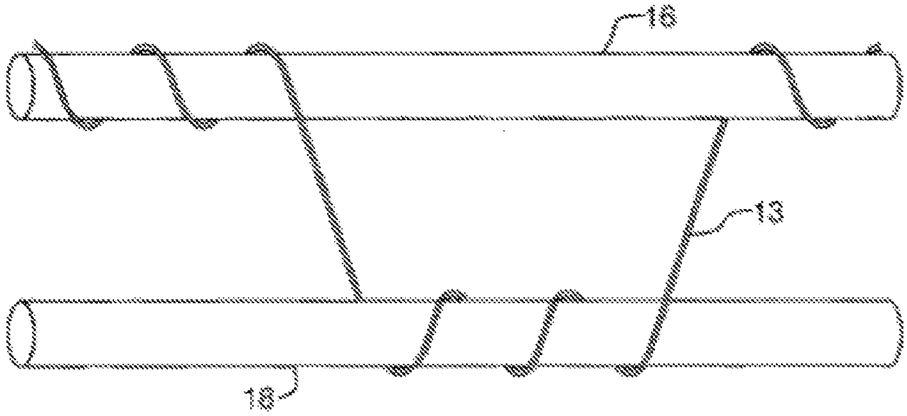
FIG. 4 is a fragmentary, side elevational view of another tube winding embodying the present invention.

One removes the centrifugal deposition by periodically reversing the sense of the coil rotation. This reverses the position of the "inner" and "outer" wall of the tube and reverses the direction (in the slug reference frame) of the centrifugal force on the particle 8 (FIG. 1). One method is to use two guide wires 16, 18. A tube 13 winds around one guide 16 in one direction, for example clockwise. Then after several rotations, the tube 13 crosses to the other guide 18 and winds around that guide 18 in the opposite sense, in this case counterclockwise, per FIG. 4.

In another embodiment (not shown), a single guide wire can be used if one wraps the tube loosely around the guide wire or even around an imaginary axis, several turns, straightens the tube, and bends it to wrap several coils around the wire or axis in the opposite sense.

Figure 5:
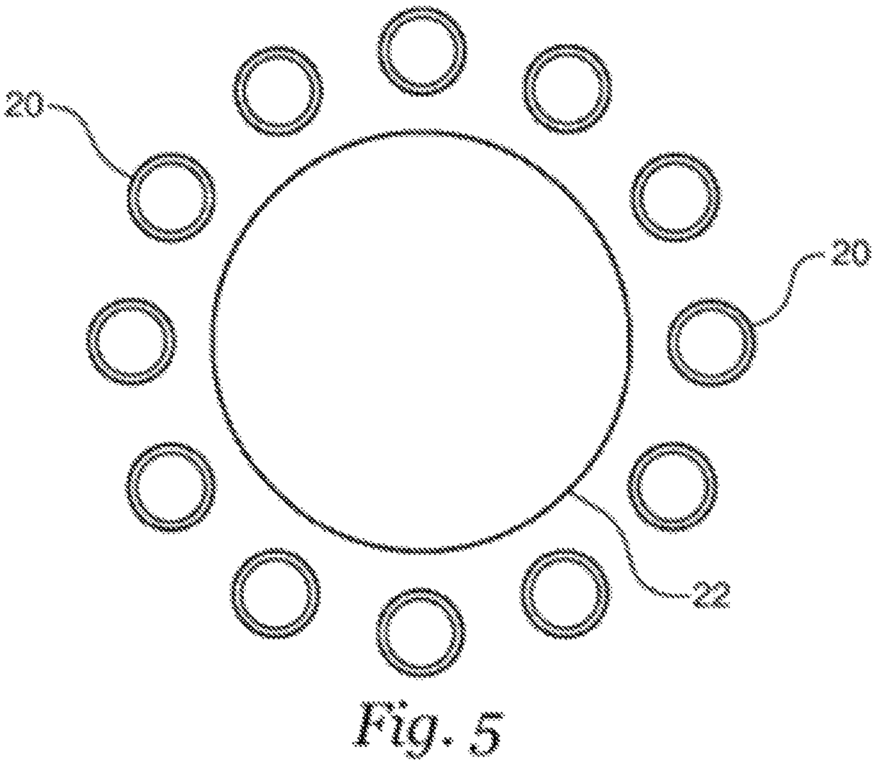
FIG. 5 is a schematic, cross-sectional view of yet another tube winding embodying the present invention.

In another embodiment, higher flows can be achieved by coiling several tubes 20 in parallel around the guide cylinder 22 or other axis, per FIG. 5.

Figure 6:
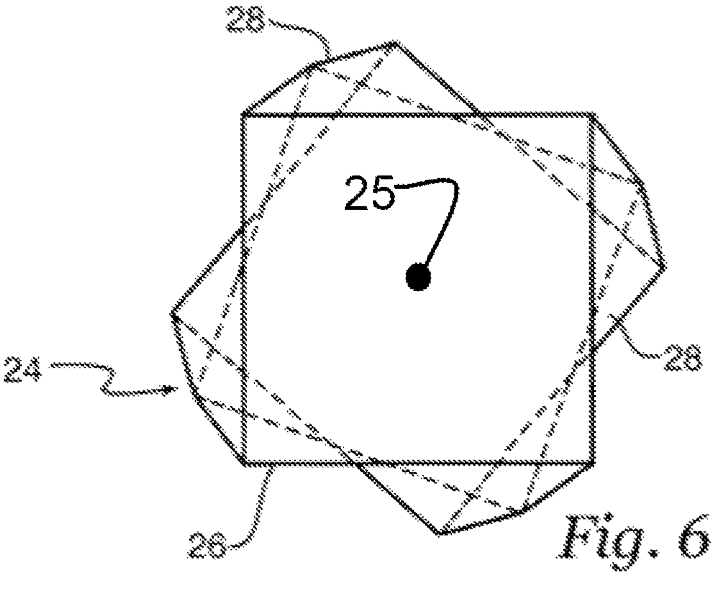
FIG. 6 is a schematic view of another aerosol unit embodying the present invention.

In yet another embodiment, per FIG. 6, the invention employs a rectangular tube 24 and no guide wire or cylinder. This implementation relies on fluid streamlines following the inner walls of the tube 24. In this version, the rectangular tube 24 bends gradually along the length of its axis 25 so that what was the bottom face 26 at the start of the tube 24 becomes the top face after some distance. The faces 26 are covered by outside walls 28. The tube 24 is thus twisted, in this manner this manner through one or more rotations, causing the zero averaging of the gravitational force on fluid slugs 10 (FIG. 1) herein following the tube streamlines. Zero averaging of the centrifugal force occurs by periodic reversing of the twist in the rectangular tube 24.

Looking at relevant equations, consider a tube of diameter d wrapped around a horizontal guide cylinder of radius R. Let the horizontal distance along the guide cylinder of a full rotation of the tube be L. The distance along the tube path to travel L along the guide is $D=((2\pi R)^2+L^2)^{1/2}$. Gravitational acceleration is g and the gravitational settling velocity is $V_{TS}$. Fluid flows through the tube at speed V. The component of the velocity along the guide axis is $V_L=V(L/D)\approx V$ if $L>>R$. The component of the velocity azimuthal to the guide is $V\phi=2\pi(R/D)V\approx 2\pi(R/L)V$. The centrifugal acceleration of a particle in the flow is $a_c=V_\phi^2/R\approx(2\pi V/L)^2R$. The terminal centrifugal velocity is $V_{TC}=V_{TS}(a_c/a_g)\approx(V_{TS}/a_g)(2\pi V/L)^2R$. The distance within the fluid slug frame a particle moves experiencing a constant gravitational force for a time t is $\delta_g=V_{TS}t$. Similarly, for a constant centrifugal force $\delta_c=V_{TC}t$. The time for the fluid to flow through one rotation is $t_g=D/V\approx L/V$ and so the maximum distance a particle is displaced by gravity is less than $\delta_{g1}=V_{TS}t_g/2\approx V_{TS}(L/V)/2$. Let N be the number of coil turns before the tube switches guides. The time for the fluid to cycle between rods (and therefore rotation sense) is $t_c=2ND/V\approx 2NL/V$ and so the maximum distance a particle is displaced by centrifugal force is less than $\delta_{c1}=V_{TS}t_c/2\approx N(V_{TS}/a_g)(2\pi)^2(V/L)R$.

The following example is intended to illustrate the present invention and should not be construed in limitation thereof.

EXAMPLE I

In operation, an aerosol transport is employed for aerosol transport through a tube across a building. The 10 μm size particles employed have a sedimentation velocity of about 0.3 cmfs. The transport distance is 100 meters, the tube diameter is 1 cm, and the guide radius is 1 cm. Let the length L (of full particle rotation in the tube) be 20 cm. Finally, let the velocity be 100 cmfs. In this case, the transit time is about 20 seconds and the Reynolds number is about 600. Let N be 2. Then the maximum displacement downward due to gravity is 0.06 cm and the maximum displacement radially due to centrifugal force is 0.12 cm.

Thus it can be seen how novel and useful the aerosol transport system of the invention is. That is, it is a means for transporting relatively large aerosol particles over long distances inside a tube to arrive at a destination with greatly reduced particle fall-out or losses due to gravity or centrifugal forces.

Commercial Applications of the aerosol transport system of the Invention are seen as follows.

Multiplexing an aerosol detector to several aerosol collectors. An example of this is the U.S. Postal Service using one aerosol detector to identify aerosols from several letter-handling machines.

Facility Protection. An example of this is placing aerosol collectors throughout a building and transporting the aerosol back to a single aerosol analysis room.

Sampling wand for bioaerosol collection in difficult to reach locations such as detecting aerosols located behind walls and within ducts.

What is claimed is:

1. A method of transporting an aerosol within a tube over a long distance, the aerosol comprising a plurality of particles in a fluid, while reducing settling of the plurality of particles, the method comprising:

rotating the fluid in a first direction about a horizontal axis of rotation while transporting the aerosol in a direction that is parallel to the horizontal axis of rotation; and rotating the fluid in a second direction about the horizontal axis of rotation, the second direction opposing the first direction while transporting the aerosol in the direction parallel to the horizontal axis of rotation to compensate for gravitational forces, centrifugal forces, or both.

2. The method of claim 1, wherein rotating the fluid in the first and second directions form countervailingly wound paths.

3. The method of claim 1, wherein a cross-section of the tube is round, angular, or rectangular.

4. An aerosol transport system comprising:

a first fluid axis extending substantially horizontally;

a first guide wire coincident with the first fluid axis;

a second fluid axis parallel to and offset from the first fluid axis;

a second guide wire coincident with the second fluid axis;

a tube having an inner wall defining a lumen configured to transport an aerosol therethrough;

a first segment of the tube wound about outer surfaces of the first guide wire along the first fluid axis; and a second segment of the tube wound about outer surfaces of the second guide wire along the second fluid axis, wherein the windings of the first and second segments compensate for forces causing a settling of particles within the tube.

5. The aerosol transport system of claim 4, wherein the first segment, the second segment, or both includes a plurality of countervailing paths.

6. The aerosol transport system of claim 4, wherein a direction of winding of the second segment opposes the direction of winding of the first segment.

* * * * *